United States Patent [19]
Rerek et al.

[11] Patent Number: 5,849,315
[45] Date of Patent: Dec. 15, 1998

[54] EMULSIFIER COMPOSITION FOR SKIN CARE FORMULATIONS

[75] Inventors: Mark Rerek, Scotch Plains, N.J.; Elliott Zucker, Shohola, Pa.; Gerhard Dahms, Velbert, Germany

[73] Assignee: ISP Investments Inc., Wilmington, Del.

[21] Appl. No.: 854,016

[22] Filed: May 8, 1997

[51] Int. Cl.$^6$ ................ A61K 7/00; A61K 9/13
[52] U.S. Cl. .......... 424/401; 514/937; 514/944; 514/938
[58] Field of Search ............... 424/401, 450; 514/437, 938, 944

[56] References Cited

U.S. PATENT DOCUMENTS 5,510,120  4/1996  Jones et al. ............... 424/499
5,560,918  10/1996  Wivell et al. ............... 424/401

*Primary Examiner*—Sally Gardner-Lane
*Attorney, Agent, or Firm*—Walter Katz; William J. Davis; Marilyn J. Maue

[57] ABSTRACT

An emulsifier composition for skin care formulations, which is present in the form of a bilayer lamellar gel network, which is stable up to a temperature of about 50° C., comprising by weight, about 3–40% of a high HLB swellant which is lecithin, and a blend of low HLB emulsifier gellants, to 100%, the blend of gellants having a resultant HLB of about 1.5 to about 5. In a skin care formulation, the lamellar gel network forms a discrete third phase between the oil and water phases.

10 Claims, No Drawings

EMULSIFIER COMPOSITION FOR SKIN CARE FORMULATIONS

BACKGROUND OF THE INVENTION

1. Field of the Invention

This invention relates to emulsifier compositions for skin care formulations, and, more particularly, to an emulsifier composition which will form a lamellar liquid crystal gel network in an oil-in-water system, thereby to provide the user a skin feel of lubricity and emollience, and skin barrier strengthening to provide moisturization without added moisturizer.

2. Description of the Prior Art

Human body skin forms a barrier which protects the body against uncontrolled loss of water. The outermost layer of the skin, the stratum corneum, provides this barrier. Traditionally, the stratum corneum has been described as a bricks-and-mortar structure in which the corneocyte "bricks" are surrounded by lipid "mortar". The lipid region is known to provide the semi-permeability barrier needed for healthy skin, and the physical organization of the lipids is known to be critical for good barrier function.

Skin lipids have been the subject of much research in recent years, and the relatively simple "mortar" model has recently evolved into a more complex "Domain Mosaic Model" (DMM). In this model, skin lipids are described as having domains of solid or gel-state lipids bordered by lipids in a more fluid liquid crystalline state called a "grain boundary".

A DMM arrangement provides an effective barrier that prevents the indiscriminate loss of water, yet allows controlled evaporation to regulate body temperature. The more fluid character of the grain boundaries represents areas where materials may diffuse in or out of the system. However, according to the DMM, lipids in the fluid grain boundaries can be lost through a process termed co-micellization detergency. Loss of any lipids from the grain boundaries disrupts the organization of stratum corneum lipids and leads to loss of barrier function. Healthy skin requires optimal barrier function and maintenance of skin moisture for prevention of irritation and dryness.

Lipid depletion eventually results in a weakened, more permeable barrier. A permeable barrier readily loses moisture, resulting in dull, dry skin. A permeable barrier is also more readily penetrated by foreign materials which can cause sensitive skin reactions.

Skin care products are formulated with emulsifiers to stabilize the oil and water phases. However, emulsifiers can interact with the skin in an antagonistic manner for the following reason. The natural tendency of most emulsifiers is to form detergent-like micelles of lipid and emulsifier. Since the lipids of the skin in the grain boundaries are oriented in a more fluid lamellar fashion, they are vulnerable to the solubilizing effects of conventional detergent-like micellar emulsifiers. This solublization can result in a net loss of lipid, thus weakening the skin's protective barrier.

In this invention, the problem of lipid loss with conventional emulsifiers is overcome by stabilizing the emulsion through a lamellar gel phase which approximates the skin's natural structure. Accordingly, the invention skin products will enhance skin lipids, rather than depleting them.

When present in oil-in-water or water-in-oil systems, conventional emulsifiers function by forming an interface with their hydrophobic portions in the oil and their hydrophilic portions in the water. Regardless of whether the emulsion is oil- or water-continuous, the system can be fundamentally described as having two phases and one interface.

In contrast, the invention emulsifier composition is balanced to produce a complex bilayer lamellar gel system. The bilayer gels herein advantageously stabilize emulsions by forming a discrete third phase between the oil and water phases. The result is a non-traditional system which can be described as having three phases and two interfaces, which is fundamentally different from the traditional two phases and one interface systems.

The lamellar gel stabilization network that is formed in the skin care composition herein thus is naturally compatible with the lamellar structure of the stratum corneum lipids.

The unique lamellar gel stabilization network of the invention composition thus builds product structure and imparts emulsion stability in two ways. First, the distinct third (lamellar) phase of the composition stabilizes the oil phase; and, secondly, it increases the viscosity of the aqueous phase.

DESCRIPTION OF THE INVENTION

The skin care formulations, and an emulsifier composition therefor, provides the user with a skin feel of lubricity and emollience, and provide moisturization without added moisturizer.

The emulsifier composition of the invention is a mixture of a high HLB emulsifier, particularly, lecithin, in a weight amount of about 3.7 to 21%, preferably 4.5 to 17%, and optimally about 6.8 to 12%, and a blend of low HLB emulsifiers, to 100%. The blend of low HLB emulsifiers has a resultant HLB of about 1.5 to 5, preferably 1.5 to 4, and, optimally about 2.5 to 3.5.

In skin care formulations, which contain water and oil components, the emulsifier composition of the invention provides and retains the desired bilayer gel network of the oil-in-water system, and its desired HLB ratios, even over a wide pH range, e.g. from 2 to 12. The HLB stabilization in the emulsifier composition provides skin care formulations which can accept acid or base components therein as an alpha hydroxy acid, or a depilatory, in the formulation.

In the preferred form of the invention, the low HLB blend of emulsifiers includes emulsifiers having a non-ionizable group, e.g. an alcohol, such as behenyl alcohol (HLB 1.9); as well as emulsifiers having an ionizable group therein, e.g. carboxyl, such as stearic acid, palmitic acid (HLB 3.2); or maleated soybean oil (HLB 1.9); or esters such as glyceryl monostearate (HLB 3.4) or sorbitan monostearate (HLB= 4.7). The skin care formulation is made by suitable mixing of about 1–10% by weight of the emulsifier composition, preferably 2–7%. In one embodiment, the gellant comprises about 8–30% behenyl alcohol, about 15–30% glyceryl monostearate, about 15–40% of a mixture of palmitic and stearic acids and 0–30% of maleated soybean oil. In another embodiment, the gellant comprises 8–27% behenyl alcohol, about 18–25% glyceryl monostearate, about 3–10% of a mixture of lauryl, myristyl and cetyl alcohols, about 18–35% of a mixture of palmitic and stearic acids and about 12–20% of maleated soybean oil.

The gel network formed by the emulsifier composition herein begins a phase transition above 45° C. Therefore, to ensure high temperature stability for the skin care formulation, it is preferred to add a small amount of a hydrocolloid stabilizer such as Stabileze® 06—International Specialty Products which is a crosslinked polyvinyl maleic anhydride/methyl vinyl ether polymer.

The invention will now be described in more detail with reference to the following examples.

The following emulsifier compositions of Examples 1–6 were prepared by mixing the several components therein thoroughly at room temperature.

| Swellant | Wt. % | Gellants | Wt. % | HLB |
|---|---|---|---|---|
| EXAMPLE 1 | | | | |
| Lecithin | 9.89 | Behenyl alcohol | 24.18 | 1.9 |
| | | Glyceryl stearate | 28.46 | 3.4 |
| | | Palmitic acid | 15.11 | 3.3 |
| | | Stearic acid | 12.36 | 3.2 |
| | | Total | 90.11 | 2.9 |
| EXAMPLE 2 | | | | |
| Lecithin | 11 | Behenyl alcohol | 23 | 1.9 |
| | | Glyceryl stearate | 21 | 3.4 |
| | | Palmitic acid | 14.85 | 3.3 |
| | | Stearic acid | 12.15 | 3.2 |
| | | Maleated soybean oil | 18 | 1.9 |
| | | Total | 89 | 2.68 |
| EXAMPLE 3 | | | | |
| Lecithin | 2 | Sorbitan stearate | 98 | 4.7 |
| EXAMPLE 4 | | | | |
| Lecithin | 9.79 | Behenyl alcohol | 24.18 | 1.9 |
| | | Glyceryl stearate | 21.98 | 3.4 |
| | | Palmitic acid | 15.11 | 3.3 |
| | | Stearic acid | 12.36 | 3.2 |
| | | Maleated soybean oil | 16.48 | 1.9 |
| | | Total | 90.21 | 2.66 |
| EXAMPLE 5 | | | | |
| Hydrogenated Lecithing | 9 | Behenyl alcohol | 24 | 1.9 |
| | | Glyceryl stearate | 24 | 3.4 |
| | | Palmitic acid | 17.2 | 3.3 |
| | | Stearic acid | 10.8 | 3.2 |
| | | Lauryl alcohol | 1.5 | 3.3 |
| | | Myristyl alcohol | 2 | 2.9 |
| | | Cetyl alcohol | 1.5 | 2.5 |
| | | Total | 91 | 2.3 |
| EXAMPLE 6 | | | | |
| Lecithin | 7 | Behenyl alcohol | 23 | 1.9 |
| | | Glyceryl stearate | 21 | 3.4 |
| | | Palmitic acid | 17.8 | 3.3 |
| | | Stearic acid | 11.7 | 3.2 |
| | | Lauryl alcohol | 1 | 3.3 |
| | | Myristyl alcohol | 1.5 | 2.9 |
| | | Cetyl alcohol | 1 | 2.5 |
| | | Maleated soybean oil | 16 | 1.9 |
| | | Total | 93 | 2.52 |

Typical skin care formulation using the emulsifier compositions of Examples 1–6 were prepared as described below in Examples 7–10.

EXAMPLE 7

| Skin Care Formulation | |
|---|---|
| Phase A | |
| Water | 67.3 |
| Glycerin | 1.0 |
| Stabileze ® QM (ISP) | 0.2 |
| Phase B | |
| Ceraphyl ® 230 (ISP) | 4.0 |
| Ceraphyl ® 494 (ISP) | 6.0 |
| Ceraphyl ® 368 (ISP) | 10.0 |
| Composition of Example 6 (ISP) | 5.0 |
| Phase C | |
| Water | 5.0 |
| NaOH (10%) | 0.5 |
| Phase D | |
| Germaben ® IIE (ISP) | 1.0 |
| Total | 100% |

Heat phase A at 70° C. until clear. Add phase B and homogenize at 70° C. With homogenization add phase C at 70° C. Allow to cool with mixing. Add phase D with mixing when temperature is 40° C. or lower.

EXAMPLE 8

| All Natural Skin Cream | |
|---|---|
| Phase A | |
| Composition of Example 4 | 5.0 |
| Sunflower oil | 3.0 |
| Almond oil | 5.0 |
| Grape seed oil | 4.0 |
| Jojoba oil | 6.0 |
| Vitamin E acetate | 2.0 |
| Phase B | |
| Glycerin | 3.0 |
| Carbopol ® 5984 (3% soln) | 3.34 |
| Water | 68.11 |
| Phase C | |
| Phenonip | 0.5 |
| Perfume (Dragoco) | 0.05 |
| Total | 100 |

Heat phases A and B to 80° C. Add A to B with continuous stirring. Homogenize 1 minute. Cool to room temperature with continuous stirring. Add phase C at room temperature.

The user experienced a skin feel of lubricity and emollience upon application of the formulation to the skin.

EXAMPLE 9

| Moisturizer Cream | |
|---|---|
| Phase A | |
| Composition of Example 5 | 4 |
| Ceraphyl ® GA-D | 2 |
| Ceraphyl ® 791 | 4 |
| Ceraphyl ® 494 | 6 |
| Ceraphyl ® 368 | 8 |
| Phase B | |
| Glycerin | 3 |
| Stabileze ® QM (1.25 wt %) | 10 |
| PVP K 30 | 1 |
| Water | 61.5 |

-continued

Moisturizer Cream

| Phase C | | |
|---|---|---|
| Phenonip | | 0.5 |
| | Total | 100 |

Heat phases A and B to 80° C. Add A to B with continuous stirring. Homogenize 1 minute. Cool to room temperature with continuous stirring. Add phase C at room temperature.

A feeling of lubricity and emollience was felt by the user.

EXAMPLE 10

SKIN CARE CREAM WITH GLYCOLIC ACID

| Ingredient | Wt. % |
|---|---|
| DI Water | 52.80 |
| Glycerin | 1.00 |
| Veegum Ultra | 1.00 |
| CMC 99-7HOF | 0.50 |
| Ceraphyl 230 | 4.00 |
| Ceraphyl 494 | 6.00 |
| Ceraphyl 368 | 10.00 |
| ProLipid 131 | 5.00 |
| DI Water | 2.00 |
| Glycolic Acid (70%) | 5.70 |
| NaOH (10% sol'n) | 11.00 |
| Germaben II-E | 1.00 |
| Total | 100.00 |

PROCEDURE

1. Combine CMC and glycerin of phase A. Sprinkle Veegum into DI with stirring at RT. Begin heating to 70°–75° C. with stirring. Add glycerin/CMC to phase A with stirring during heating.
2. Combine phase B, heat to 75°–80° C., stir until uniform.
3. When phase A uniform and stirring at 70°–75° C. and phase B is uniform at 75°–80° C., add phase B to phase A with homogenizer and turn off heat. When batch thickens, switch to sweep agitation for cool-down.
4. Add phase C with sweep agitation at 40° C.
5. Add phase D with sweep agitation at 35° C.
6. Make up for water loss, sweep to RT.

While the invention has been described with particular reference to certain embodiments thereof, it will be understood that changes and modifications may be made which are within the skill of the art. Accordingly, it is intended to be bound only by the following claims, in which:

What is claimed is:

1. An emulsifier composition for use in skin care formulations, which is present in the form of a bilayer lamellar gel network which approximates the natural structure of skin, and is stable up to a temperature of about 50° C., comprising, by weight, about 3–40% of a high HLB swellant which is lecithin, and a blend of HLB emulsifier gellants, to 100%, the blend of said gellants having a resultant HLB of about 1.5 to about 5, and comprises, about 8–30% behenyl alcohol, about 15–30% glyceryl monostearate, about 15–40% of a mixture of palmitic and stearic acids and 0–30% of maleated soybean oil.

2. A composition according to claim 1 wherein said lecithin is present in the composition in an amount of about 4.5–17%.

3. A composition according to claim 1 wherein said lecithin is present in the composition in an amount of about 6.8–12%.

4. A composition according to claim 1 wherein the resultant HLB of the gellants is about 1.5 to about 4.

5. A composition according to claim 1 wherein the resultant HLB of the gellants is about 2 to about 3.

6. A composition according to claim 1 comprising about 4.5–17% lecithin, and wherein the emulsifier gellant blend comprises about 8–27% behenyl alcohol, about 18–25% glyceryl monostearate, about 18–35% of a mixture of palmitic and stearic acids, about 3–10% of a mixture of lauryl, myristyl and cetyl alcohols, and about 12–20% of maleated soybean oil, in which said blend has an HLB of about 1.5–4.

7. A composition according to claim 6 in which said blend has an HLB of about 2–3.

8. A skin care formulation having a skin feel of lubricity and emollience in the absence of an added moisturizer comprising, by weight, about 1–10% of the emulsifier composition of claim 1 which is present in the form of a lamellar gel network, and water and suitable oil components to form an oil-in-water system wherein said lamellar network forms a discrete third phase between said oil and water phases.

9. A skin care formulation according to claim 8 containing about 2–7% of said emulsifier composition.

10. A skin care formulation according to claim 8 containing about 3–5% of said emulsifier composition, about 50–80% water and about 15–45% of said oil component.

* * * * *